United States Patent [19]

Watt

[11] 4,384,582
[45] May 24, 1983

[54] PATIENT PLATE FOR DIATHERMY APPARATUS, AND DIATHERMY APPARATUS FITTED WITH IT

[75] Inventor: John H. Watt, London, England

[73] Assignee: DRG (UK) Ltd., Bristol, England

[21] Appl. No.: 155,168

[22] Filed: Jun. 2, 1980

[51] Int. Cl.³ .............................................. A61B 17/36
[52] U.S. Cl. ................................ 128/303.13; 128/798
[58] Field of Search ..................... 128/303.13, 303.14, 128/303.17, 783, 798, 802, 803, 792

[56] References Cited

U.S. PATENT DOCUMENTS

| | | | |
|---|---|---|---|
| 1,973,387 | 9/1934 | Neymann et al. | 128/792 |
| 3,972,329 | 8/1976 | Kaufman | 128/641 |
| 3,998,215 | 12/1976 | Anderson et al. | 128/641 |
| 4,114,263 | 9/1978 | Szpur | 128/641 |
| 4,117,846 | 10/1978 | Williems | 128/303.13 |
| 4,303,073 | 12/1981 | Archibald | 128/303.13 |

FOREIGN PATENT DOCUMENTS

| | | | |
|---|---|---|---|
| 73065 | 2/1917 | Austria . | |
| 104861 | 12/1926 | Austria . | |
| 478672 | 7/1929 | Fed. Rep. of Germany . | |
| 1965195 | 12/1969 | Fed. Rep. of Germany . | |
| 2239596 | 2/1974 | Fed. Rep. of Germany | 128/798 |
| 2414812 | 8/1979 | France | 128/303.13 |
| 429486 | 5/1935 | United Kingdom . | |
| 479735 | 2/1938 | United Kingdom . | |
| 502167 | 3/1939 | United Kingdom . | |
| 514466 | 11/1939 | United Kingdom . | |
| 823946 | 11/1959 | United Kingdom . | |
| 1118644 | 7/1968 | United Kingdom . | |
| 1256603 | 12/1971 | United Kingdom . | |
| 1264673 | 2/1972 | United Kingdom . | |
| 1288323 | 9/1972 | United Kingdom . | |
| 1296550 | 11/1972 | United Kingdom . | |
| 1333573 | 10/1973 | United Kingdom . | |
| 1372404 | 10/1974 | United Kingdom . | |
| 1378246 | 12/1974 | United Kingdom . | |
| 1441622 | 7/1976 | United Kingdom . | |
| 1488957 | 10/1977 | United Kingdom . | |
| 1512248 | 5/1978 | United Kingdom . | |

Primary Examiner—Lee S. Cohen
Attorney, Agent, or Firm—Larson and Taylor

[57] ABSTRACT

An aluminium foil electrode 11 is secured to a flexible insulating sheet 10 by pressure sensitive adhesive. The foil has a slot 14 extending for the major portion of the foil's length from a contact edge 12b. To test for cracks in the foil which might cause poor electrical contact with the patient and thus cause diathermy burns, the resistance around the U-shaped pathway from the contact edge on one side of the slot to the other side of the slot is monitored.

The adhesive is exposed through the slot 14 and through cut-out apertures 15,15a in the foil 11, to improve contact of the patient plate with the patient. A removable cover sheet 16 protects the exposed adhesive when not in use.

12 Claims, 4 Drawing Figures

PATIENT PLATE FOR DIATHERMY APPARATUS, AND DIATHERMY APPARATUS FITTED WITH IT

FIELD OF THE INVENTION

The present invention relates to a diathermy electrode.

DESCRIPTION OF PRIOR ART

Diathermy or electrosurgery is a technique in which living tissue is cut and/or coagulated by means of a high frequency alternating electrical current. It is in widespread use in many types of surgical procedure. The alternating current passed through the tissue is of radio frequency, typically of the order of 500 kHz to 1.75 MHz and the cutting and/or coagulation results primarily from heat generated as a result of tissue resistance to the passage of the current. Cutting is effected by passage of a sinusoidal current which causes the cells to dehydrate and explode rapidly to give a clean incision. Coagulation is effected by passage of a current having a damped pulse wave form which causes more thermal heating and brings about slower dehydration of the cells resulting in coagulation.

Diathermy is carried out by application to a patient of two electrodes one of which is held by the surgeon (the active electrode) while the other returns the current to earth (the return, neutral or indifferent electrode or "patient plate").

The amount of heat communicated to the patient by each electrode depends on the size thereof, the smaller electrode imparting the greater amount of heat because it produces a higher current density. In diathermy, therefore, the active electrode is usually small and the patient plate is large. It is desirable for the patient plate to make electrical contact with a large area of the patient's skin otherwise there may be excessive skin heating resulting in burns. Diathermy machines are therefore typically equipped with a patient circuit safety monitoring system connected to the patient plate and arranged to give an alarm signal in the event of abnormal patient contact conditions.

Details of prior art electrodes (some for diathermy and some for other uses) can be seen from U.K. Patent Specifications Nos. 429486, 479735, 502167, 514466, 823946, 1296550 and 1378246.

Until recently the commonly used patient plate consisted of a lead plate wrapped in saline-soaked gauze and strapped to the patient's leg or some other part of the body. This arrangement was inconvenient and suffered from the disadvantage that if the gauze dried out during the operation a severe burn could result. An electrode using a similar principle is seen in U.K. Specification No. 1118644. More recently used patient plates are disposable or of limited life and comprise metal foil, for example on a base of sheet material such as plastics, paper or cardboard.

Such foil type patient plates can be seen for example in U.K. Specification Nos. 1256603, 1264673, 1333573, 1372404, 1441622, 1488957 and 1512248.

However these foil patient plates can also give rise to problems. In particular there is difficulty in ensuring that a sufficient area of the plate is in contact with the patient, wrinkling or distortion thereof significantly reducing the area of contact. Also cracks in the foil can break the electrical connection to a large area of the plate and render that area inoperative without completely destroying the electrical contact to the patient. Such cracks arise because a single patient plate is often used for a number of different patients and the plate has to be removed from one patient, straightened and then applied to another patient. The repeated bending and flexing of the foil together with the removal process is liable to give rise to fatigue cracks. Thus foil type patient plates can also cause burns. Moreover, a clamp has to be provided to connect the disposable foil electrode to the diathermy apparatus and it is necessary to ensure a good connection between the clamp and the electrode, or else an earth return path may occur through another part of the patient's body.

A solution to this latter problem is shown in U.K. Specification 1288323. The clamp makes not one but two electrical connections to the patient plate, and before use a low voltage DC current is passed through the plate between these connections. If no current flows, one or other connection is faulty. The drawing shows a small U-shaped cut-out in the patient plate between the connections, but its purpose is not described and since it only extends a very short distance into the patient plate it cannot help to show whether the whole plate is in a satisfactory condition for making contact with the patient. A similar principle is seen in U.K. Specification No. 1264673.

U.K. Specification No. 1333573 shows a patient plate with two areas of foil on an insulating base. The two foil areas have a gap between them so that they are electrically isolated from each other. Normally, they are connected in parallel in the high frequency circuit through the patient's body, but to test the connections both with the diathermy apparatus and with the patient, a low potential is connected across the respective connections from the apparatus to the two foil areas and the resistance in the circuit thus formed through the patient's body is measured. This therefore shows if the electrical connection through the body is poor, but does not provide a direct indication of whether the electrode is usable. Moreover the test can only be made when the patient plate is connected to the patient, and if the test results are not satisfactory the patient plate has to be removed again and another one fitted. A similar patient plate is shown in U.K. Specification No. 1372404 and a pick-up electrode with some resemblance but intended for electrocardiogram apparatus is described in U.K. Specification No. 1441622.

SUMMARY OF THE INVENTION

It is an object of the invention to provide a disposable patient plate for diathermy apparatus which is inexpensive to manufacture and is safe in use.

In one aspect the present invention provides a patient plate for diathermy apparatus, comprising a sheet of flexible electrically insulating material, and a metal foil secured to one face of the sheet of insulating material, the metal foil having a contact edge for connection to diathermy apparatus, a slot in the foil extending from the contact edge towards an opposing edge of the foil for a major portion of the distance between said edges, whereby the foil defines a generally U-shaped pattern.

Preferably foil is secured to the insulating sheet by a pressure sensitive adhesive. The slot then functions both to expose an underlying area of adhesive to promote contact between the electrode to the skin and to enable cracks in the electrode to be detected more readily. The crack detector functions by means of a monitoring circuit provided in the diathermy machine and arranged to make electrical contact with the plate to either side of the slot and respond to changes of electrical resistance through the U-shaped pathway therebetween. Further apertures in the metal foil may provide additional exposed areas of adhesive which further promote contact between the electrode and the skin.

The assembly of insulating material and foil may be protected prior to use by means of a layer of release-coated sheet material.

In a second aspect the present invention provides a patient plate for diathermy apparatus, comprising a sheet of flexible electrically insulating material, a coating of pressure sensitive adhesive on one face thereof, and a metal foil secured to said face by the adhesive, the metal foil having at least one cut-out portion to expose the coating of adhesive, whereby in use the coating adheres the patient plate to the patient.

BRIEF DESCRIPTION OF THE DRAWINGS

An embodiment of the invention will now be described by way of example, with reference to the accompanying drawings, in which.

DESCRIPTION OF PREFERRED EMBODIMENTS

Figure 1:
FIG. 1 is an end view of an electrode assembly and protective sheet.
Figure 2:
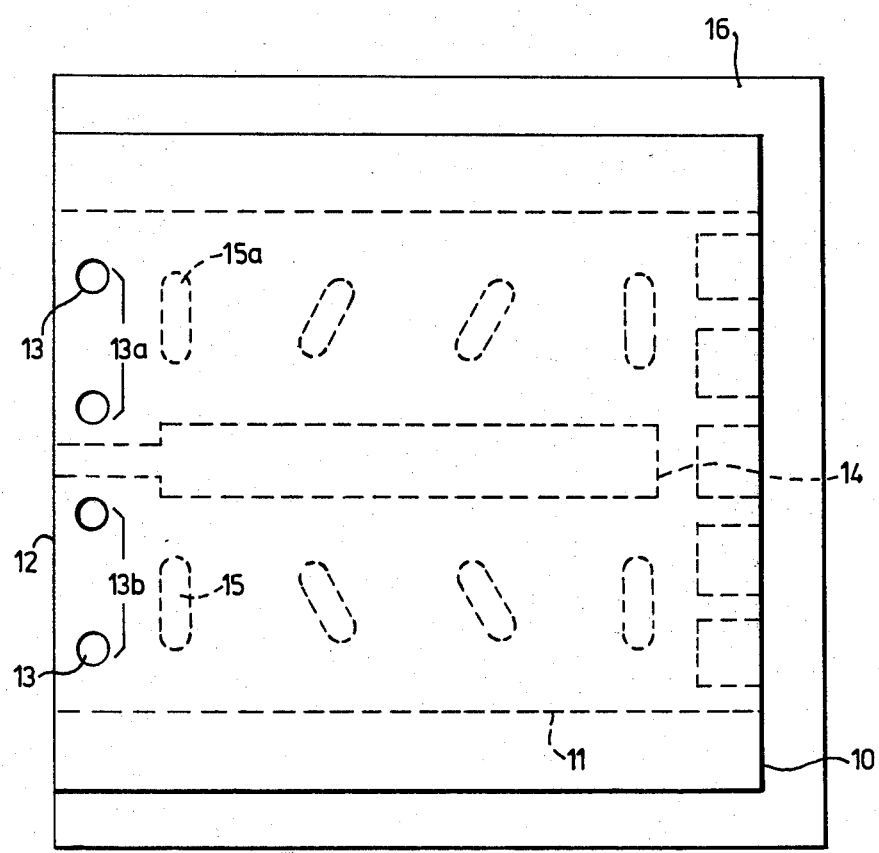
FIG. 2 is a plan view of an electrode assembly.
Figure 3:
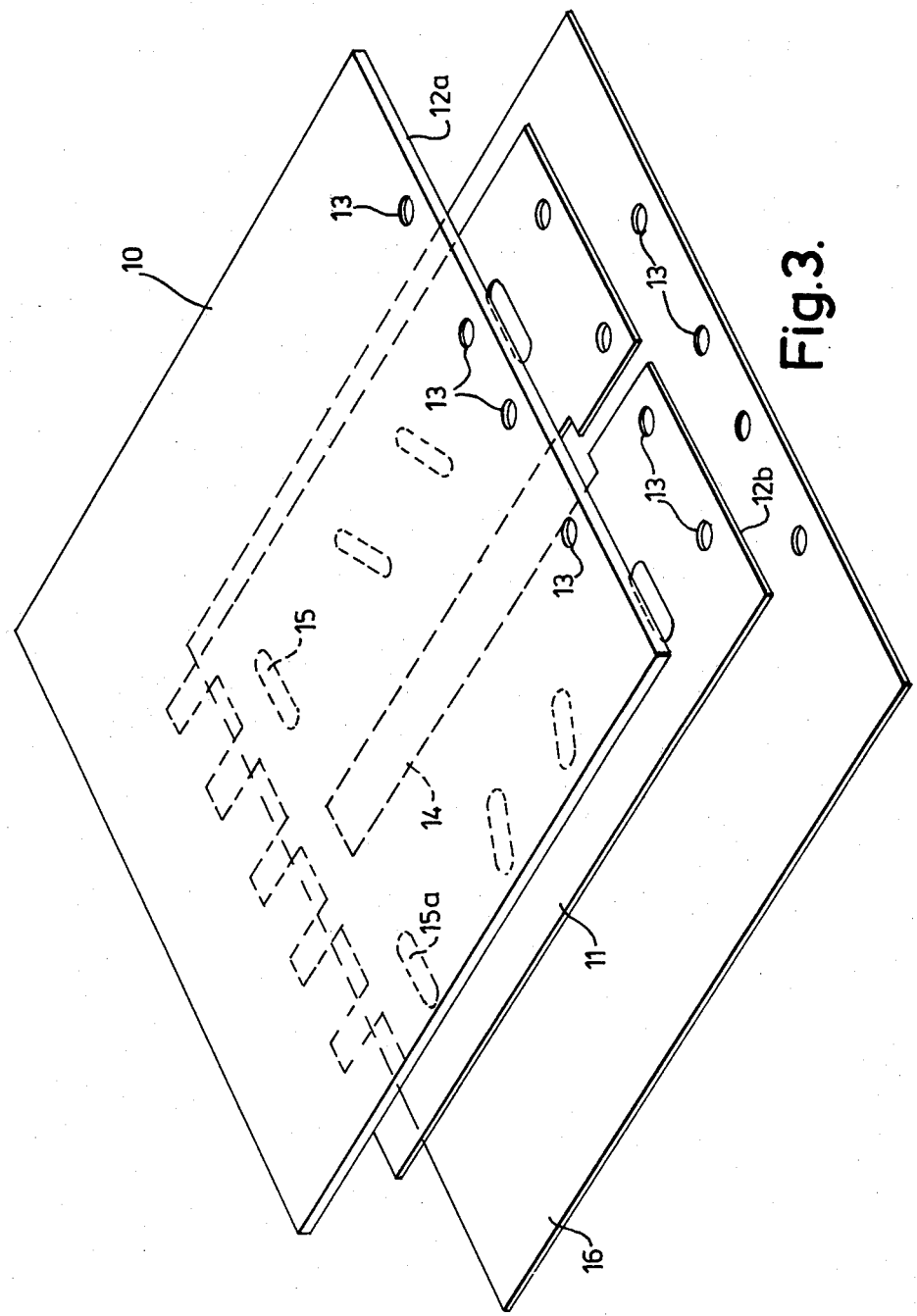
FIG. 3 is an oblique exploded view of the electrode assembly.

A generally rectangular sheet of electrically insulating flexible foamed plastics material 10 typically a closed cell polyvinyl chloride foam such as is marketed under the trade name INSEAL is coated on one face with a hypo-allergenic pressure sensitive adhesive to which is adhered a rectangular aluminium foil electrode 11 of slightly smaller length and width than the plastics sheet and of area about 200 sq. cms. An end edge 12a on the foam plastics sheet is positioned in register with a side edge 12b on the electrode to define a common contact edge having perforations 13 dimensioned and positioned to receive fastening studs of a patient plate holder (not shown) of a diathermy apparatus. Extending longitudinally in the electrode from the contact edge for a major portion of the electrode's length is a slot 14 and to either side of the slot there are apertures 15 and 15a perforated through the foil and disposed in rows. As shown in FIGS. 1-3, slot 14 and apertures 15 are free of the metal foil such that, in use, the metal foil having a generally U-shaped pattern provides substantially the entire conducting area to the patient. It will also be apparent that, in use, the face of the sheet of insulating material, in the area of slot 14 and apertures 15, is exposed to the patient. The adhesive is exposed around the edges of the foil and through the slot 14 and apertures 15,15a, and in use adheres to the patient's skin to maintain good contact between the electrode and the skin. Prior to use the electrode and insulating sheet are covered by means of a cover sheet 16 of release coated paper, which protects the exposed areas of adhesive.

Figure 4:
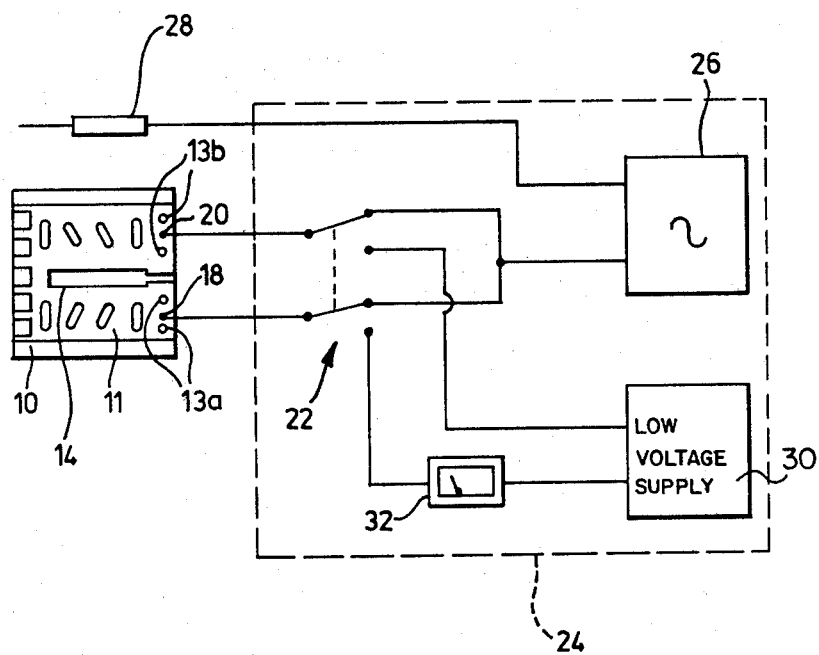
FIG. 4 is a schematic diagram of diathermy apparatus using the electrode assembly.

In use the protective cover sheet 16 is peeled off and the electrode is fitted into the patient plate holder (not shown), a first electrical contact being established in a region 18 between the perforations 13a to one side of the slot 14 and a second electrical contact being established in a region 20 between the perforations 13b to the other side of the slot (see FIG. 4). The patient plate holder is connected to a double pole switch 22 in diathermy apparatus 24. When the switch is in the normal position shown in FIG. 4, both regions 18 and 20 of the electrode 11 are connected in parallel to a conventional source 26 of high frequency current for the diathermy, the circuit being completed through the patient's body and an active diathermy electrode 28. When the switch is changed over, however, the contact regions are connected in series in a circuit having a low voltage supply 30 and a resistance monitoring meter 32. The electrical pathway between the first and second contact regions 18,20 is generally U-shaped and extends to the far edge of the electrode. It will be appreciated that the electrical resistance between the first and second contact points is sensitive to cracks in the electrode and the degree of sensitivity is increased because the slot 14 causes the pathway therebetween to be indirect and extend throughout the body of the electrode. Accordingly, the meter 32 provides a direct indication of the condition of the foil 11.

Various modifications may be made to the embodiment described above without departing from the invention. For example the cellular insulating material may be replaced by a sheet of flexible non-woven textile material. The aluminium foil used may be laminated to a very thin plastics foil, the resulting laminated material being contacted with the coating of tacky or pressure sensitive material on the sheet of flexible insulated material. The use of aluminium foil laminated to plastics foil rather than to aluminium foil alone enables the thickness of the aluminium layer to be reduced. For example, the total thickness of the laminated material may be 14 microns of which about 10 microns accounts for the aluminium layer. Such a material gives greater conformity to the patient's body and helps to increase the area of contact. The schematic diagram of the diathermy apparatus 24 is given purely by way of example, and many other configurations are possible.

The patient plate described above has the advantages that it is easy and convenient to apply and is formed in soft pliable material for added patient safety. The insulating backing sheet protects the operating theatre staff against accidental shocks. Furthermore the plate can be fitted to patient plate holders of existing diathermy machines.

I claim:

1. A patient plate for diathermy apparatus, comprising a sheet of flexible electrically insulating material, and a metal foil secured to one face of the sheet of insulating material, the metal foil having a contact edge for connection to diathermy apparatus, a slot in the foil extending from the contact edge towards an opposing edge of the foil for a major portion of the distance between said edges, whereby the foil defines a generally U-shaped pattern, said slot being free of said foil such that, in use, the metal foil having a generally U-shaped pattern provides substantially the entire conducting area to the patient, and such that, in use, the face of said sheet of insulating material, in the area of said slot, is exposed to the patient.

2. A patient plate according to claim 1 in which there is a coating of pressure sensitive adhesive on said face of the sheet of insulating material, by which the foil is secured to the insulating sheet, the coating being exposed at least through the slot whereby in use the coating adheres the patient plate to the patient.

3. A patient plate according to claim 2 wherein apertures are provided in the foil to either side of the slot, further areas of said coating being exposed through the apertures.

4. A patient plate according to claim 2 having a removable protective sheet over the foil on said face of the insulating sheet, covering the exposed coating.

5. A patient plate according to claim 1 wherein the insulating sheet is a sheet of closed cell polyvinyl chloride foam.

6. A patient plate according to claim 1 wherein the metal foil is an aluminium foil.

7. In diathermy apparatus, the combination of a patient plate and resistance monitoring means, the patient plate comprising a sheet of flexible electrically insulating material, and a metal foil secured to one face of the sheet of insulating material, the metal foil having a contact edge for connection to diathermy apparatus, a slot in the foil extending from the contact edge towards an opposing edge of the foil for a major portion of the distance between said edges, whereby the foil defines a generally U-shaped pattern, the resistance monitoring means being connected to the contact edge of the foil on each side of the slot so as to monitor the resistance of the U-shaped pattern defined by the foil.

8. Diathermy apparatus according to claim 7 in which there is a coating of pressure sensitive adhesive on said face of the sheet of insulating material, by which the foil is secured to the insulating sheet, the coating being exposed at least through the slot whereby in use the coating adheres the patient plate to the patient.

9. Diathermy apparatus according to claim 8 wherein apertures are provided in the foil to either side of the slot, further areas of said coating being exposed through the apertures.

10. Diathermy apparatus according to claim 8 wherein said patient plate has a removable protective sheet over the foil on said face of the insulating sheet, covering the exposed coating.

11. Diathermy apparatus according to claim 7, wherein the insulating sheet is a sheet of closed cell polyvinyl chloride foam.

12. Diathermy apparatus according to claim 7, wherein the metal foil is an aluminium foil.

* * * * *